United States Patent
Kirenko et al.

(10) Patent No.: US 9,770,213 B2
(45) Date of Patent: Sep. 26, 2017

(54) DEVICE, SYSTEM AND METHOD FOR EXTRACTING PHYSIOLOGICAL INFORMATION

(71) Applicant: KONINKLIJKE PHILIPS N. V., Eindhoven (NL)

(72) Inventors: Ihor Olehovych Kirenko, Veldhoven (NL); Erik Bresch, Eindhoven (NL); Mukul Julius Rocque, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 151 days.

(21) Appl. No.: 14/831,033

(22) Filed: Aug. 20, 2015

(65) Prior Publication Data
US 2016/0120482 A1 May 5, 2016

(30) Foreign Application Priority Data
Oct. 30, 2014 (EP) .................................... 14190978

(51) Int. Cl.
*A61B 5/00* (2006.01)
*A61B 5/024* (2006.01)
*A61B 5/1455* (2006.01)

(52) U.S. Cl.
CPC ........ *A61B 5/7278* (2013.01); *A61B 5/02416* (2013.01); *A61B 5/02427* (2013.01);
(Continued)

(58) Field of Classification Search
CPC .............. A61B 5/7278; A61B 5/02416; A61B 5/02427; A61B 5/7221; A61B 5/0077; A61B 5/14551
See application file for complete search history.

(56) References Cited

U.S. PATENT DOCUMENTS 6,334,065 B1 * 12/2001 Al-Ali .................... A61B 5/746
600/323
2007/0263226 A1 11/2007 Kurtz et al.
(Continued)

OTHER PUBLICATIONS

Chen, T.; Hyperspectral Imaging for the Remote Sensing of Blood Oxygenation and Emotions; 2012; Cranfield University. 176 pages.
(Continued)

*Primary Examiner* — Catherine Voorhees

(57) ABSTRACT

The present invention relates to a device, system and a method for extracting physiological information indicative of at least one vital sign of a subject from detected electromagnetic radiation reflected from the subject. The device comprises an input interface for receiving a data stream of detection data derived from detected electromagnetic radiation reflected from a skin region of a subject, wherein the detected electromagnetic radiation is detected by a polarized radiation detector, while the polarization angle of the polarized radiation detector is changed, a PPG extraction unit for extracting a photoplethysmographic, PPG, signal from said detection data, a signal quality determination unit for determining quality metrics from said PPG signal for different settings of the polarization angle of the polarized radiation detector, a selection unit for selecting the optimum quality metric value from the determined quality metrics and for generating polarization control information for use by said polarized radiation detector for setting the polarization angle to an angle value, at which said optimum quality metric value was obtained, for subsequent detection of radiation, and a processor for deriving physiological information indicative of at least one vital sign from the PPG signal.

16 Claims, 4 Drawing Sheets

(52) U.S. Cl.
CPC .......... *A61B 5/7221* (2013.01); *A61B 5/0077* (2013.01); *A61B 5/14551* (2013.01)

(56) References Cited

U.S. PATENT DOCUMENTS

| | | | |
|---|---|---|---|
| 2009/0082642 A1* | 3/2009 | Fine | A61B 5/0059 600/300 |
| 2009/0226071 A1* | 9/2009 | Schuler | A61B 5/02416 382/133 |
| 2010/0210951 A1 | 8/2010 | Rahman et al. | |
| 2012/0203086 A1 | 8/2012 | Rorabaugh et al. | |
| 2013/0076932 A1 | 3/2013 | Chhibber et al. | |
| 2013/0088612 A1 | 4/2013 | Imai | |
| 2013/0307950 A1 | 11/2013 | Aharon | |
| 2014/0243622 A1 | 8/2014 | Crowe et al. | |

OTHER PUBLICATIONS

Fujikake, H., et al.; Electrically-Controllable Liquid Crystal Polarizing Filter for Eliminating Reflected Light; 1998; Optical Review; 5(2)93-98.

Verkruysse, W., et al.; Remote plethysmographic imaging using ambient light; 2008; Optical Express; 16(26) 21434-21445.

Wieringa, F. P., et al.; Contactless Multiple Wavelength Photoplethsmographic Imaging: A First Step Toward SpO2 Camera Technology; 2005; Annals of Biomedical Engineering; 33(8)1034-1041.

* cited by examiner

DEVICE, SYSTEM AND METHOD FOR EXTRACTING PHYSIOLOGICAL INFORMATION

CROSS REFERENCE TO RELATED APPLICATIONS

This application claims the benefit of European provisional application serial no. 14190978.8 filed Oct. 30, 2014, which is incorporated herein by reference.

FIELD OF THE INVENTION

The present invention relates to a device, system and method for extracting physiological information indicative of at least one vital sign of a subject from detected electromagnetic radiation reflected from a subject, such as a person or animal.

BACKGROUND OF THE INVENTION

Vital signs of a person, for example the heart rate (HR), the respiration rate (RR) or the arterial blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow.

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Using PPG technology, vital signs can be measured, which are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations, with severe motion, challenging environmental illumination conditions, or high required accuracy of the application, where an improved robustness and accuracy of the vital sign measurement devices and methods is required, particularly for the more critical healthcare applications.

Camera-based vital signs measurement in the presence of specular reflectance can cause a lot of errors and it is desirable to use only those regions for measurement that do not contain specular reflectance. Ideally, the negative impact of specular reflectance can be suppressed by using a dedicated illumination and a camera with perfect cross polarization. A photoplethysmograph device applying this approach is disclosed in US 2014/243622 A1. Such ideal system assumes that there are no other sources of (non-polarized) light. However, in practice, it is almost impossible to provide only one perfectly cross-polarized illumination source, since there is always some uncontrolled ambient illumination present.

US 2007/263226 A1 discloses a tissue imaging system for examining the medical condition of tissue having an illumination optical system, which comprises a light source beam shaping optics, and polarizing optics. An optical beam splitter directs illumination light to an imaging sub-system, containing a spatial light modulator array. An objective lens images illumination light from the spatial light modulator array to the tissue. An optical detection system images the spatial light modulator to an optical detector array. In an embodiment crossed polarizers, in particular a drive prepolarizer in the path of the illumination light and a polarization analyzer in the path of the detected light, are used which are rotated in unison so that their extinction axes rotate into various positions relative to the tissue. By a controller they are rotated by the same angular amount so that they remain crossed to ensure that specularly reflected light and light re-emerging from the tissue while nominally retaining the initial polarization state are both eliminated by the crossed polarization analyzer, whereas light that re-emerges from the tissue with its polarization rotated to some extent by the birefringent structures within the tissue can then have some portion of the light transmitted through the polarization analyzer. In this way, the polarization sensitive optics enable the imaging of the birefringent tissue structures.

US 2013/307950 A1 discloses a method for probing morphology of a tissue surface using a system which may include a light source, a polarizer, an analyzer, and a camera with a plurality of picture elements. The method illuminates the tissue surface with incident light through the polarizer. The camera may capture through the analyzer, scattered light from the tissue surface in a continuous sequence of image frames. Variation of polarization state may be of at least one of the incident light from the light source by varying the polarizer or the scattered light from the tissue surface by varying the analyzer. During the capture, for a picture element of the camera, a varying intensity signal of the scattered light is detected responsive to the varying polarization state.

SUMMARY OF THE INVENTION

It is an object of the present invention to provide a device, system and method for extracting physiological information indicative of at least one vital sign of a subject from detected electromagnetic radiation reflected from the subject, which minimize or even completely suppress the negative effect of specular reflection on the measurement.

In a first aspect of the present invention, a device for extracting physiological information indicative of at least one vital sign of a subject from detected electromagnetic radiation reflected from a subject is presented, said device comprising:
  an input interface for receiving a data stream of detection data derived from detected electromagnetic radiation reflected from a skin region of a subject, wherein the detected electromagnetic radiation is detected by a polarized radiation detector, wherein the polarization angle of the polarized radiation detector is changed during the detection of the electromagnetic radiation,
  a PPG extraction unit for extracting a photoplethysmographic, PPG, signal from said detection data,
  a signal quality determination unit for determining quality metrics from said PPG signal for different settings of the polarization angle of the polarized radiation detector,
  a selection unit for selecting the optimum quality metric value from the determined quality metrics and for generating a polarization control information for use by said polarized radiation detector for setting the polarization angle to an angle value, at which said optimum quality metric value was obtained, for subsequent detection of radiation, and
  a processor for deriving physiological information indicative of at least one vital sign from the PPG signal.

In a further aspect of the present invention, a system for extracting physiological information indicative of at least one vital sign of a subject from detected electromagnetic radiation reflected from the subject is presented, said system comprising:
  a device as disclosed herein and
  a polarized radiation detector for detecting electromagnetic radiation reflected from a skin region of a subject and for deriving detection data from the detected electromagnetic radiation, wherein said polarized radiation detector is configured to change the polarization angle during the detection of the electromagnetic radiation either to different angle values to find the optimum angle value or to an optimum angle value in response to polarization control information received from said device.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

The present invention is based on the idea to provide for automated adjustment of the polarization angle of the polarized radiation detector, e.g. a camera including or being provided with a polarizer, to minimize an impact of specular reflectance, improve the effect of cross polarization in the presence of an ambient light, and even reduce or totally overcome the need of a dedicated, dominant cross-polarized illumination.

As mentioned above, PPG measurement can be performed using a detector, such as a camera, much similar to how this is realized in a contact sensor, i.e. by measuring the light reflected back from the skin of a subject. This light is modulated by the pulsatile arteries and the modulation amplitude contains the information of the blood saturation levels. This modulation can be seen in the detection data, e.g. an image sequence of subsequently acquired image frames (e.g. video data acquired by a video camera). The amplitude is measured in units of pulsatility and is computed from the spatial pixel average of a region of interest from the image data.

Pulsatility only occurs in that fraction of the light that has penetrated into the skin and is diffusely reflected. The specularly reflected light reaching the detector does not contain any light modulation due to arterial blood pulsatility since it is the light reflected back from the surface of the skin. This causes a decrease in the pulsatility observed. But also in other quality metrics than the pulsatility the effect of specular reflection can be observed, such as the signal-to-noise ratio (SNR) or the shape information.

This effect is exploited according to the present invention by automatically adjusting the polarization angle of the polarized radiation detector to reduce an impact of specular reflectance from uncontrolled ambient illumination by finding the optimum quality metric value of the used quality metrics of a measured PPG signal by optimizing (e.g. maximizing) the quality metrics. Hereby, the "optimum" is to be understood in the respect of the quality of the extracted signal (which may be the quality of PPG signals, as well as a quality of the final extracted vital signal (e.g. SpO2) calculated as a derivative of PPG signals), which shall be highest.

Generally, the interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (i.e. a living being) and derivative parameters. In particular, the term "vital sign" comprises blood volume pulse-signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), skin temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or maybe even about the temperature, etc.).

The term "physiological information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For obtaining a physiological information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

In a preferred embodiment of the proposed device said PPG extraction unit is configured to extract two or more PPG signals from detection data derived from detected electromagnetic radiation reflected from two or more different skin regions of the subject, said signal quality determination unit is configured to determine quality metrics from each of said two or more PPG signals, and said selection unit is configured to separately select the optimum quality metric value from the determined quality metrics for each of said two or more PPG signals and to generate a polarization control information for use by said polarized radiation detector for setting the polarization angle to angle values, at which said optimum quality metric value was obtained for the respective PPG signal, for subsequent detection of radiation from the respective skin region. It has been found that the optimum polarization angle may be different for different regions of interest, i.e. for different skin areas. Hence, it is advantageous to determine the optimum polarization angle separately for each skin area for use in the detection of radiation from the respective skin area.

In another embodiment of the proposed device said PPG extraction unit, said signal quality determination unit and said selection unit are configured to regularly, continuously or from time to time perform their functions to regularly, continuously or from time to time adjust the polarization angle setting. Since the conditions of the ambient light and/or the position and orientation of the subject change from time to time it is preferred to update the setting of the polarization angle at least from time to time to maintain the quality and accuracy of the measurement over time.

In still another embodiment of the proposed device said PPG extraction unit is configured to extract two or more PPG signals from different frequency components of said detection data, said signal quality determination unit is configured to determine quality metrics from each of said two or more PPG signals, and said selection unit is configured to separately select the optimum quality metric value from the determined quality metrics for each of said two or more PPG signals and to generate a polarization control information for use by said polarized radiation detector for setting the polarization angle to angle values, at which said optimum quality metric value was obtained for the respective PPG signal, for subsequent detection of radiation in the respective frequency range. Different frequency components may e.g. be different color components such as green, red and blue light, or red and infrared light components. For each of the respective frequency component a different setting of the polarization angle may thus be used for the detection of radiation since the specular reflection may differently affect the different frequency components. This further optimizes the measurement and the quality of the obtained physiological information.

This can e.g. be achieved by using a radiation detector, e.g. a camera, comprising separate detection units, e.g. image sensors (for instance, for each color channel). A polarizer in front of each of detection units (image sensors) may be adjusted separately. In a different embodiment a single detection unit (image sensor) may be used, with which a time sequential processing can be used for subsequent detection of radiation in different frequency ranges.

There are different signals or pieces of information that may be used as quality metrics. In a preferred embodiment said signal quality determination unit is configured to determine pulsatility, signal-to-noise ratio and/or shape information as quality metrics from said PPG signal for different settings of the polarization angle of the polarized radiation detector. SNR values provide an indication of the strength of the extracted PPG signal compared to noise (caused by ambient light, specular reflectance, motion, etc.). Maximum SNR value would correspond to a maximum pulsatility of the PPG signal and a minimum level of noise. The shape of a pulse signal, contained in the shape information, corresponds to "cleanness" of a frequency spectrum; noise induced by specular reflectance would introduce extra frequency, and therefore would corrupt the shape of the PPG signal.

In a preferred embodiment the pulsatility is used as quality metric. Accordingly, said signal quality determination unit is configured to determine pulsatility as quality metrics from said PPG signal for different settings of the polarization angle of the polarized radiation detector and wherein said selection unit is configured to select the maximum pulsatility value from the determined pulsatility values and for generating a polarization control information for use by said polarized radiation detector for setting the polarization angle to an angle value, at which said maximum pulsatility value was obtained, for subsequent detection of radiation.

For changing the polarization angle of the polarized radiation detector various embodiments exist. For instance, in one embodiment the detector may comprise a mechanically or electrically controllable polarizer, whose polarization angle can be mechanically or electrically changed. In another embodiment the detector may comprise a rotatable polarizer, whose polarization angle can be changed by rotation of the polarizer, arranged in front of the detector input, at which the electromagnetic radiation is received. Still further, in an embodiment the detector may comprises an optical structure, whose polarization angle can be electrically controlled, arranged in front of the detector input, at which the electromagnetic radiation is received.

In another embodiment said input interface is configured to receive a polarization angle information indicating the setting of the polarization angle of the polarized radiation detector during the detection of the electromagnetic radiation or said signal quality determination unit is configured to determine the polarization angle information from the detected electromagnetic radiation. Thus, there are different options available to provide the information about the current polarization angle to the device.

Preferably, the proposed system further comprises a non-polarized radiation detector, such as an additional imaging unit, e.g. a second camera, for detecting electromagnetic radiation reflected from the same skin region of the subject as the polarized radiation detector and for deriving additional detection data from the detected electromagnetic radiation, wherein said device is configured to use said additional detection data as reference data used for selecting the optimum quality metric value from the determined quality metrics and for generating said polarization control information. This reference data may e.g. be used to extract a reference PPG signal for comparison with the (original) PPG signal. This may speed up the process of finding the optimum quality metric value for the optimizing the polarization angle, for instance it may reduce the amount of iterations needed to find an optimal polarization angle.

In still another embodiment said non-polarized radiation detector comprises a plethysmography sensor, configured for being mounted to a skin portion of the subject for acquiring photo-plethysmography signals and/or an imaging unit for acquiring a sequence of image frames of the subject over time, from which photo-plethysmography signals for use a reference data can be derived.

BRIEF DESCRIPTION OF THE DRAWINGS

These and other aspects of the invention will be apparent from and elucidated with reference to the embodiments described hereinafter. In the following drawings.

DETAILED DESCRIPTION OF THE INVENTION

Figure 1:
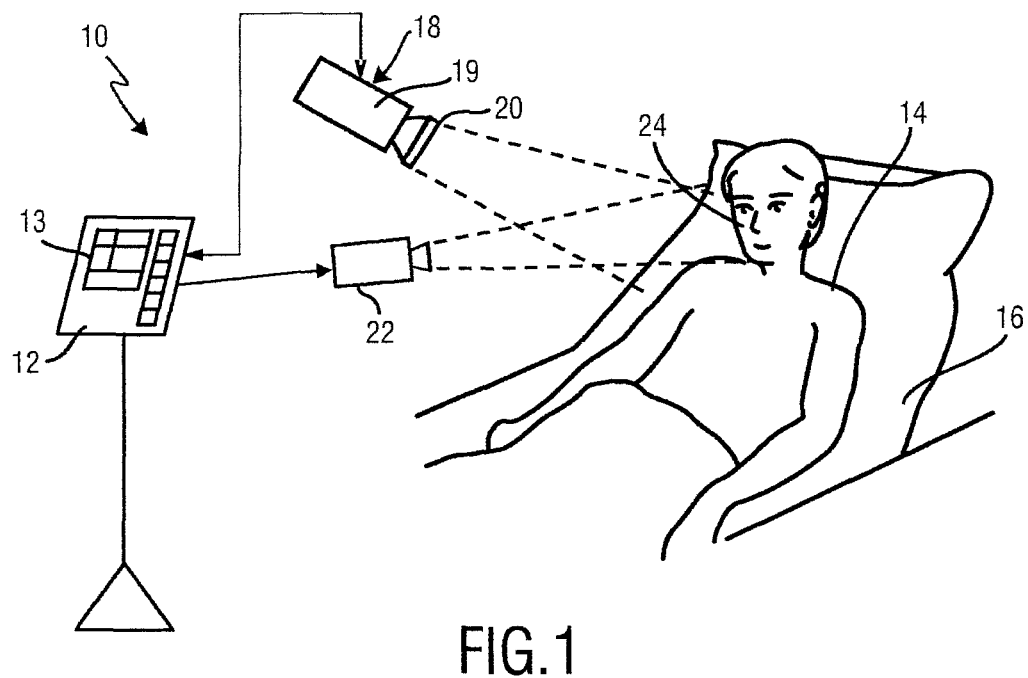
FIG. 1 shows a schematic diagram of a first embodiment of a system according to the present invention.

FIG. 1 shows a schematic diagram of a system 10 according to the present invention including a device 12 for extracting physiological information indicative of at least one vital sign of a subject 14 from detected electromagnetic radiation reflected from the subject 14. The subject 14, in this example a patient, lies in a bed 16, e.g. in a hospital or other healthcare facility, but may also be a neonate or premature infant, e.g. lying in an incubator, or person at home or in a different environment, such as a nursing home.

A polarized radiation detector 18 is provided for detecting electromagnetic radiation reflected from a skin region 24 (also called region of interest (ROI)) of the subject 14 and for deriving detection data from the detected electromagnetic radiation. The polarized radiation detector 18 is configured to change the polarization angle during the detection of the electromagnetic radiation either to different angle values to find the optimum angle value or to an optimum angle value in response to polarization control information from the device 12 as will be explained below in more detail.

The detector 18 preferably comprises a camera 19 (also referred to as imaging unit, or as camera-based or remote PPG sensor) including a suitable photosensor for (remotely and unobtrusively) capturing image frames of the subject 14, in particular for acquiring a sequence of image frames of the subject 14 over time, from which photo-plethysmography signals can be derived. The image frames captured by the camera 19 may particularly correspond to a video sequence captured by means of an analog or digital photosensor, e.g. in a (digital) camera. Such a camera 19 usually includes a photosensor, such as a CMOS or CCD sensor, which may also operate in a specific spectral range (visible, IR) or provide information for different spectral ranges. The camera 19 may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements.

The detector 18 further preferably comprises (internal or external) polarization adjustment means 20 for changing the polarization angle during the detection of the electromagnetic radiation so that only radiation having a particular polarization angle is allowed to transmit and reach the radiation detection elements of the detector, such as the photosensor of the camera 19.

When using a camera 19 the system 10 may further optionally comprise a light source 22 (also called illumination source), such as a lamp, for illuminating a region of interest 24, such as the skin of the patient's face (e.g. part of the cheek or forehead), with light, for instance in a predetermined wavelength range or ranges (e.g. in the red, green and/or infrared wavelength range(s)). The light reflected from said region of interest 24 in response to said illumination is detected by the detector 18. In another embodiment no dedicated light source is provided, but ambient light is used for illumination of the subject 14. From the reflected light only light in a desired wavelength range (e.g. green light) may be detected and/or evaluated.

The device 12 is further connected to or provided with an interface 13 for displaying the determined information and/or for providing medical personnel with an interface to change settings of the device 12, the detector, the light source 22 and/or any other parameters of the system 10. Such an interface 13 may comprise different displays, buttons, touchscreens, keyboards or other human machine interface means.

A system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, or the like. The uni- or bidirectional communication between the device 12, the detector 18, and the interface 13 may work via a wireless or wired communication interface. Other embodiments of the present invention may include a device 12, which is not provided standalone, but integrated into the detector 18 or the interface 13.

Figure 2:
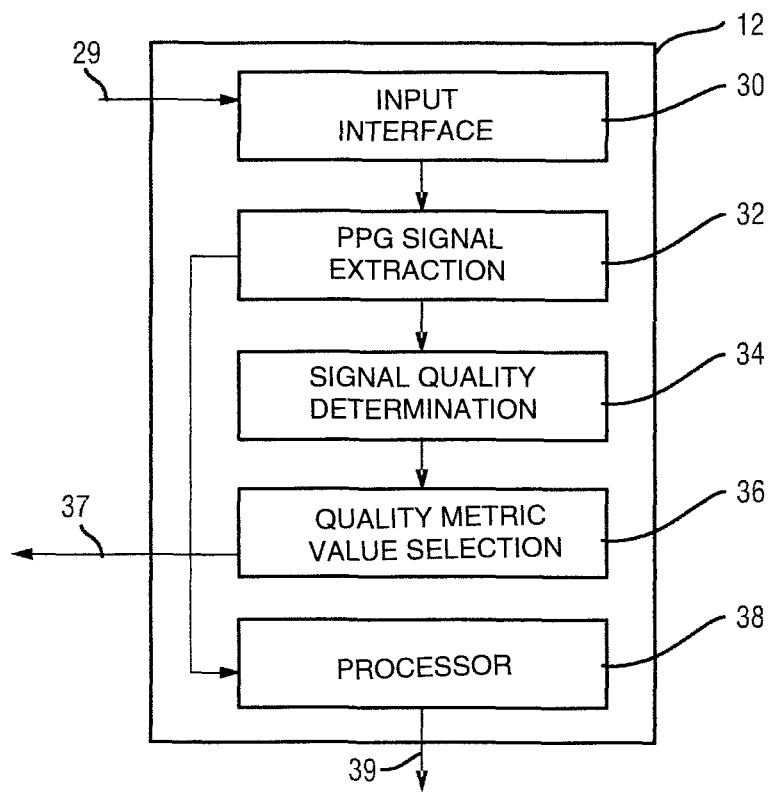
FIG. 2 shows a schematic diagram of a device according to the present invention.

FIG. 2 shows a more detailed schematic illustration of an embodiment of the device 12 according to the present invention. The device 12 comprises an input interface 30 for receiving a data stream 29 of detection data derived from detected electromagnetic radiation reflected from a skin region of a subject 14 as detected and provided by the polarized radiation detector 18, wherein the polarization angle of the polarized radiation detector is changed during the detection of the electromagnetic radiation (i.e. while the polarization angle of the polarized radiation detector is changed), at least in an initial calibration or optimization stage in which the optimum polarization angle shall be determined.

The device 12 further comprises a PPG extraction unit 32 for extracting a photoplethysmographic (PPG) signal from said detection data 29. The way to obtain PPG signals from detected electromagnetic radiation, e.g. from images of a region of interest, is generally known in the field of remote photoplethysmography, e.g. from the above described documents, and shall thus not be explained in more detail here.

A signal quality determination unit 34 is provided for determining quality metrics from said PPG signal for different settings of the polarization angle of the polarized radiation detector. Various quality metrics can be used for this purpose. For instance, the signal quality determination unit 34 may be configured to determine pulsatility, signal-to-noise ratio and/or shape information as quality metrics from said PPG signal for different settings of the polarization angle of the polarized radiation detector.

A selection unit 36 selects the optimum quality metric value from the determined quality metrics and generates polarization control information 37 for use by said polarized radiation detector for setting the polarization angle to an angle value, at which said optimum quality metric value was obtained, for subsequent detection of radiation. Thus, for subsequent radiation detection and evaluation a particular setting of the polarization angle is used, which may be updated from time to time or regularly or continuously.

From the PPG signal, derived from radiation with the optimized setting of the polarization angle, a processor 38 derives physiological information 39 indicative of at least one vital sign. For instance, one or more of a heart rate signal, a breathing rate signal, the SpO2 rate, etc. can be derived as desired in the particular application.

The radiation that is detected by the detector 18 is modulated by the pulsatile arteries and the modulation amplitude contains the desired physiological information, e.g. the information of the blood saturation levels. This modulation can be seen in the data stream 29 of detection data, e.g. a camera video, with the amplitude measured in units of pulsatility (mNP) and may be computed from the spatial pixel average of a region of interest from the data stream 29, e.g. the video data.

Various options exist for providing the signal quality determination unit 34 with information about the current setting of the polarization angle of the polarized radiation detector. In one option the polarization angle is controlled, e.g. by a computer or a controller, which may be coupled with the device 12, in particular the signal quality determination unit 34 so that the information about the current polarization angle can be directly provided to the signal quality determination unit 34. For instance, a control signal for controlling the polarizer or an electronic position signal indicating the current (rotational position) of the polarizer may be provided. Hence, the input interface 30 may receive a polarization angle information indicating the setting of the polarization angle of the polarized radiation detector during the detection of the electromagnetic radiation.

As another option the polarization angle can be measured, e.g. by measuring the current rotational position of the polarizer 20 or by measuring the polarization of detected radiation, and by forwarding the measured information to the signal quality determination unit 34. Hence, the signal quality determination unit 34 may determine the polarization angle information from the detected electromagnetic radiation.

In the following, details of the invention will be explained by referring to the detection of light as a particular example of detected radiation, for instance of detect visible light and infrared light (preferably near-infrared light).

Figure 3:
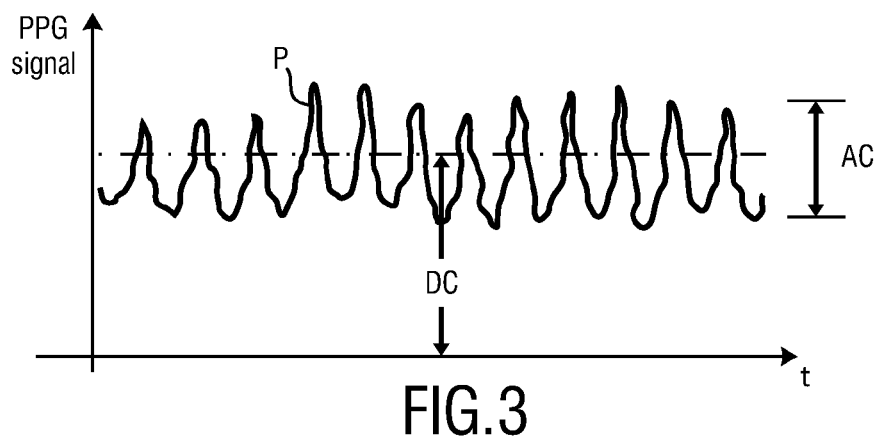
FIG. 3 shows a diagram illustrating the computation of pulsatility.

FIG. 3 shows a diagram illustrating the computation of pulsatility. FIG. 3 particularly shows a PPG signal P, which may represent the measured signal of a single pixel or the averaged signal of a group of pixels. The pulsatility of said PPG signal P is defined as the amplitude of the AC signal part of the PPG signal normalized to the DC level of the PPG signal P. Pulsatility only occurs in that fraction of the light that has penetrated into the skin and is diffusely reflected. The specularly reflected light reaching the detector 18 does not contain any light modulation due to arterial blood pulsatility since it is the light reflected back from the surface of the skin. This causes a decrease in the pulsatility observed. The effect of specular reflectance can be shown with a sample computation as shown in Table 1.

TABLE 1

|  | DC (LSB) | AC (LSB) | Pulsatility (mNP) |
|---|---|---|---|
| Without Specular reflectance | 100 | 1 | 10 |
| With Specular reflectance (+10%) | 110 | 1 | 9.09 |

As shown in Table 1, the amount of specular reflectance can affect the value of pulsatility with an inverse relationship on the pulsatility (the more the specular reflectance, the lesser the pulsatility). The pulsatility of skin regions showing specular reflectance will thus have a lower pulsatility, whereas skin regions where there is no specular reflectance will have a higher pulsatility.

Figure 4A:
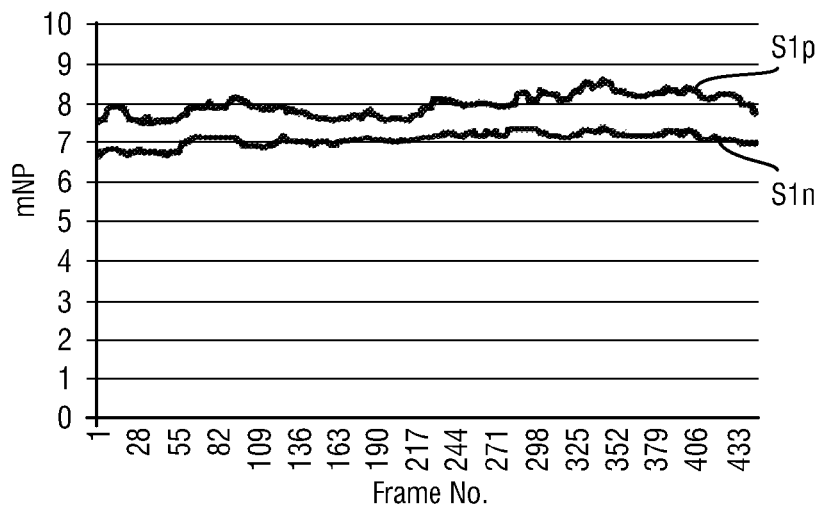
FIG. 4A shows a diagram illustrating the effect of specular reflectance on pulsatility from a skin region showing specular reflectance.
Figure 4B:
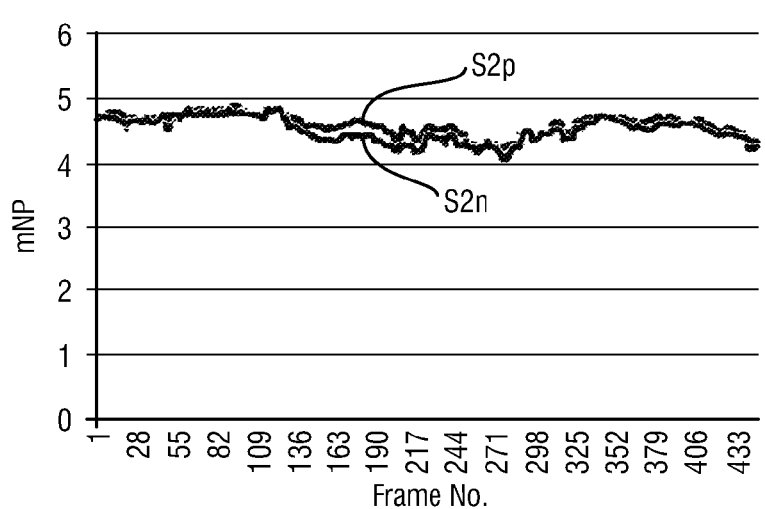
FIG. 4B shows a diagram illustrating the effect of specular reflectance on pulsatility from a skin region showing no specular reflectance.

FIG. 4 shows diagrams illustrating the effect of specular reflectance on pulsatility. Pulsatility (mNP) measurement signals S1p, S2p obtained by a polarized detector and pulsatility measurement signals S1n, S2n obtained by a non-polarized detector are particularly depicted. The pulsatility measurement signals S1p, S1n shown in FIG. 4A are obtained from a skin region showing specular reflectance and the pulsatility measurement signals S2p, S2n shown in FIG. 4B are obtained from a skin region showing no specular reflectance. As can be seen in FIG. 4, there is a significant difference in the pulsatility measure of the region of specular reflectance whereas there is hardly any difference in regions of no specular reflectance.

According to a preferred embodiment of the present invention the polarization angle of the detector 18 is defined as an optimal polarization angle (for a part of the ROI or entire ROI) if a pulsatility of extracted PPG signal (in a part of the ROI or entire ROI) is maximum for this polarization angle compared to other polarization angles of the adjustable polarizer 20. Since the ambient light might consist of light from various illumination sources, with different angles of reflectance, and the skin area is not flat, the optimal polarization angle might be different for different parts of ROI. Therefore, another variation of this embodiment of the present invention selection of a spatially local polarization angle of the adjustable polarizer is proposed to maximize the pulsatility of the PPG signal in this spatially local area.

As polarization adjustment means 20 various elements can be used. In one embodiment a mechanically or electrically controllable polarizer may be used, whose polarization angle can be mechanically or electrically changed. The polarizer may e.g. be a disk-like element or a rotatable polarizer that is mounted in front of the detector input, e.g. the lens of the camera 19, and that can be mechanically rotated, e.g. by use of a motor or actuator. In still another embodiment an optical structure may be used, whose polarization angle can be electrically controlled, arranged in front of the detector input, at which the electromagnetic radiation is received. The polarization properties of such an optical structure can be electrically controlled. As an example, liquid crystal optical elements may be used as e.g. disclosed in Fujikake et al "Electrically-Controllable Liquid Crystal Polarizing Filter for Eliminating Reflected Light", Optical Review March/April, 1998, Volume 5, Issue 2, pp. 93-98.

Figure 5:
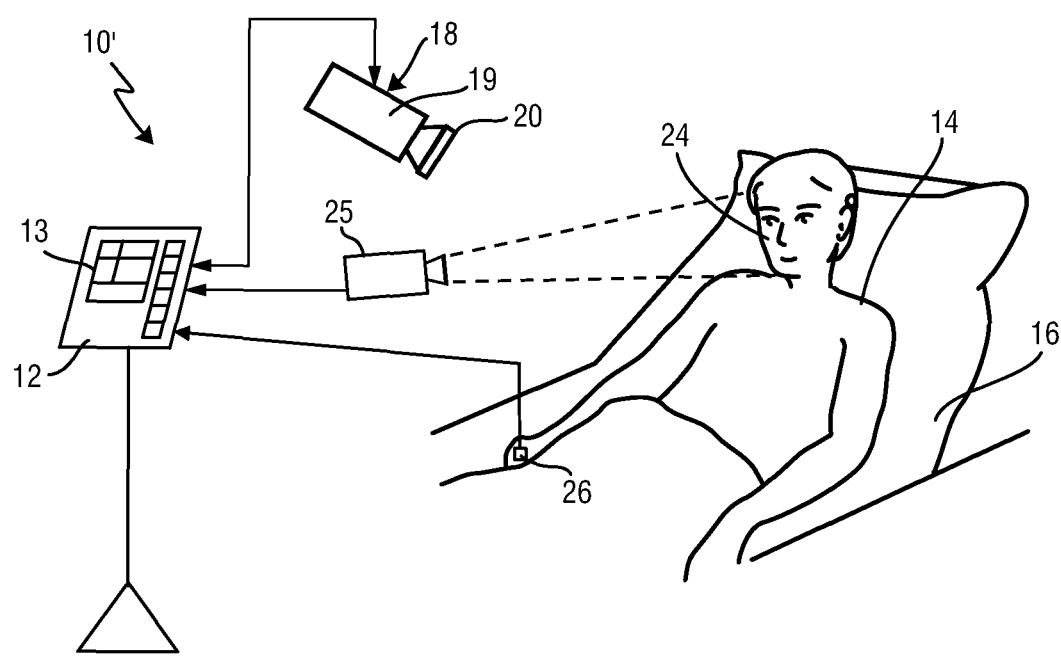
FIG. 5 shows a schematic diagram of a second embodiment of a system according to the present invention.

FIG. 5 shows a schematic diagram of a second embodiment of a system 10' according to the present invention. In this embodiment the system 10' further comprises a non-polarized radiation detector for detecting electromagnetic radiation reflected from the same skin region of the subject as the polarized radiation detector 18 and for deriving additional detection data from the detected electromagnetic radiation. The device 12 is configured to use said additional detection data as reference data used for selecting the optimum quality metric value from the determined quality metrics and for generating said polarization control information. Normally, absolute values of pulsatility of a PPG signal might vary from person to person, and have different values for various body locations. Moreover, the PPG pulsatility may change over time due to physiological reasons. Therefore, having another source of a PPG signal can be used during the optimization of the polarization angle as a sort of a "base" signal to compare with. That might reduce the number of iterations required to select the optimal polarization angle.

In one embodiment said non-polarized radiation detector comprises a plethysmography sensor 26 that is mounted to a skin portion of the subject for acquiring photo-plethysmography signals. In another embodiment said non-polarized radiation detector comprises an imaging unit 25 for acquiring a sequence of image frames of the subject over time, from which photo-plethysmography signals for use as reference data can be derived. Thus, in one embodiment of the proposed system 10', one camera 25 has no polarization and is used as a reference, while the detector 18 including the second camera 19 has a (rotating) polarizer 20 with adjustable polarization angle.

Figure 6:
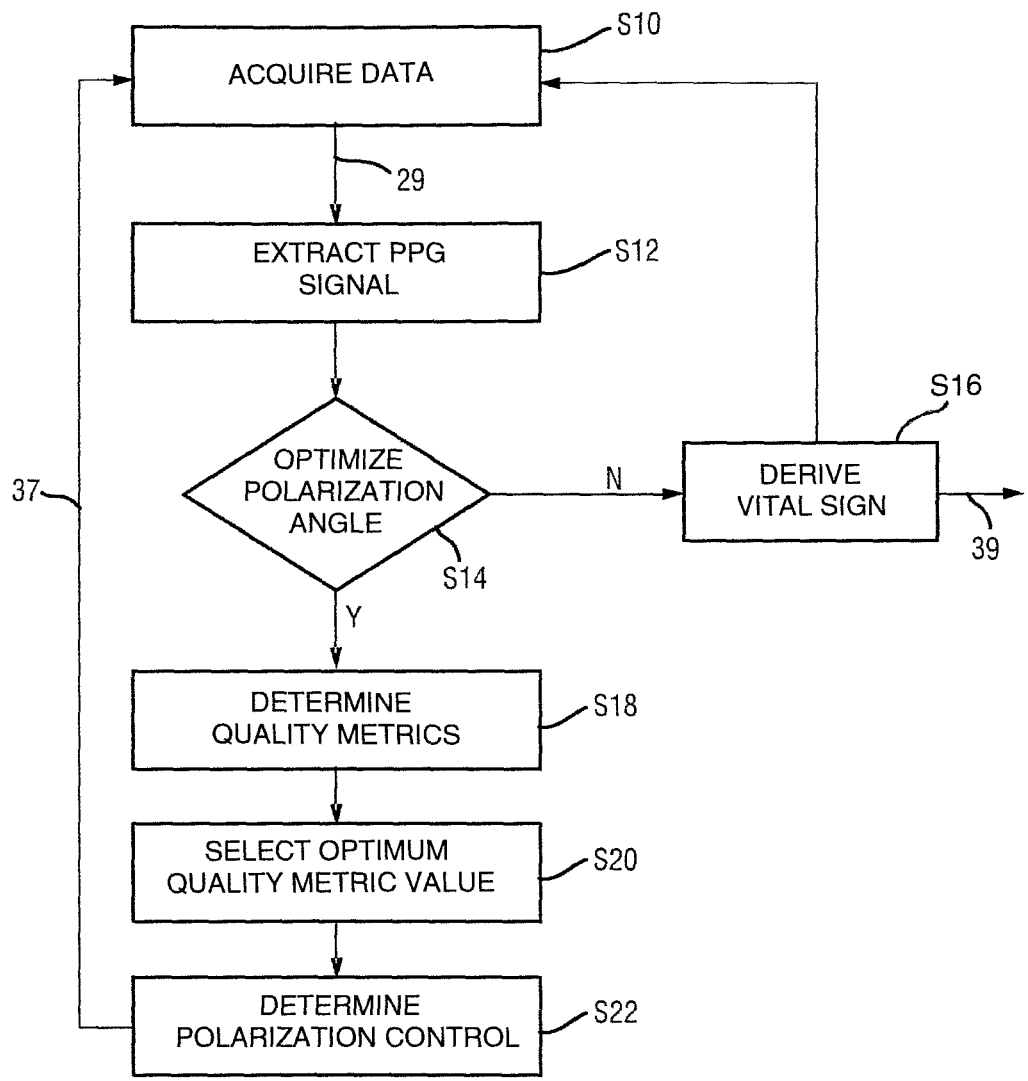
FIG. 6 shows a flow chart of an embodiment of a method according to the present invention.

A flow chart of a method according to the present invention as carried out by a system 10 shown in FIG. 1 is depicted in FIG. 6. In a first step S10 the detection data 29 are acquired by the polarized radiation detector 18, which are provided to the device 12 for processing. In a second step S12 a PPG signal is extracted from said detection data 29. In a third step S14 it is checked if said PPG signal may be used for extracting physiological information or if the polarization angle of the polarized radiation detector shall be optimized (or at least checked if the currently used polarization angle is optimal) to avoid any negative effects of specular reflection. The conditions under which it is decided to optimize the polarization angle may include that a certain time is over, the PPG signal quality has dropped, an indication has been found that the used ROI contains specular reflection, etc.

If no optimization shall be made, physiological information 39 indicative of at least one vital sign is derived from the PPG signal in step S16. The algorithm then returns to step S10, which corresponds to the embodiment, where the optimal quality level is estimated based on a final extracted vital signal, derived from PPG.

If an optimization shall be made, in step S18, quality metrics are determined from said PPG signal for different settings of the polarization angle of the polarized radiation detector 18. Further, in step S20, the optimum quality metric value is selected from the calculated quality metrics. Still further, in step S22, polarization control information 37 is determined for use by said polarized radiation detector 18 for setting the polarization angle to an angle value, at which said optimum quality metric value was obtained, for subsequent detection of radiation. The algorithm then returns to step S10 for the next iteration.

It shall be noted that other quality metrics may be used instead of the pulsatility, such as signal-to-noise ratio and/or shape information.

In summary, the present invention uses a quality metrics, such as PPG pulsatility, as a criterion for selection of an optimal polarization angle of camera polarization. Further, an embodiment uses the possibility to have several optimal polarization angles of orientation of polarizer, each of which is optimal for a spatially local part of skin area. A single camera with a computer-controlled rotating polarizer may be used to carry out image acquisitions with different polarization settings in a time-sequential manner. Therefore, a computer may control a mechanically orientable polarizer in front of the single camera, e.g., by means of an electric motor. The polarization direction can vary fast when compared with the observed photoplethysmography signal, e.g., at 5 Hz, and it would be followed by a coherent demodulation of the acquired image series. Other options include a pseudo-random sampling of polarization directions.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for extracting physiological information indicative of at least one vital sign of a subject from detected electromagnetic radiation reflected from the subject, said device comprising:
   an input interface for receiving a data stream of detection data from a polarized radiation detector for detecting electromagnetic radiation reflected from a skin region of a subject, wherein the detected electromagnetic radiation is detected while a polarization angle of the polarized radiation detector is changed,
   a PPG extraction unit for extracting a photoplethysmographic, PPG, signal from said detection data,
   a signal quality determination unit for determining quality metrics from said PPG signal for different settings of the polarization angle of the polarized radiation detector,
   a selection unit for selecting the optimum quality metric value from the determined quality metrics and for generating polarization control information for use by said polarized radiation detector for setting the polarization angle to an angle value, at which said optimum quality metric value was obtained, for subsequent detection of radiation, and
   a processor for deriving physiological information indicative of at least one vital sign from the PPG signal.

2. The device as claimed in claim 1,
   wherein said PPG extraction unit is configured to extract two or more PPG signals from detection data derived from detected electromagnetic radiation reflected from two or more different skin regions of the subject,
   wherein said signal quality determination unit is configured to determine quality metrics from each of said two or more PPG signals, and
   wherein said selection unit is configured to separately select the optimum quality metric value from the calculated quality metrics for each of said two or more PPG signals and to generate a polarization control information for use by said polarized radiation detector for setting the polarization angle to angle values, at which said optimum quality metric value was obtained for the respective PPG signal, for subsequent detection of radiation from the respective skin region.

3. The device as claimed in claim 1,
   wherein said PPG extraction unit, said signal quality determination unit and said selection unit are configured to regularly, continuously or from time to time perform their functions to regularly, continuously or from time to time adjust the polarization angle setting.

4. The device as claimed in claim 1,
   wherein said PPG extraction unit is configured to extract two or more PPG signals from different frequency components of said detection data,
   wherein said signal quality determination unit is configured to determine quality metrics from each of said two or more PPG signals, and
   wherein said selection unit is configured to separately select the optimum quality metric value from the calculated quality metrics for each of said two or more PPG signals and to generate a polarization control information for use by said polarized radiation detector for setting the polarization angle to angle values, at which said optimum quality metric value was obtained for the respective PPG signal, for subsequent detection of radiation in the respective frequency range.

5. The device as claimed in claim 1,
   wherein said signal quality determination unit is configured to determine pulsatility, signal-to-noise ratio and/or shape information as quality metrics from said PPG signal for different settings of the polarization angle of the polarized radiation detector.

6. The device as claimed in claim 1,
   wherein said signal quality determination unit is configured to determine pulsatility as quality metrics from said PPG signal for different settings of the polarization angle of the polarized radiation detector and wherein said selection unit is configured to select the maximum pulsatility value from the determined pulsatility values and for generating a polarization control information for use by said polarized radiation detector for setting the polarization angle to an angle value, at which said maximum pulsatility value was obtained, for subsequent detection of radiation.

7. The device as claimed in claim 1,
   wherein said input interface is configured to receive a polarization angle information indicating the setting of the polarization angle of the polarized radiation detector during the detection of the electromagnetic radiation or wherein said signal quality determination unit is configured to determine the polarization angle information from the detected electromagnetic radiation.

8. A system for extracting physiological information indicative of at least one vital sign of a subject from detected electromagnetic radiation reflected from the subject, said system comprising:
   a device as claimed in claim 1 and
   a polarized radiation detector for detecting electromagnetic radiation reflected from a skin region of a subject and for deriving detection data from the detected electromagnetic radiation, wherein said polarized radiation detector is configured to change the polarization angle during the detection of the electromagnetic radiation either to different angle values to find the optimum angle value or to an optimum angle value in response to polarization control information received from said device.

9. The system as claimed in claim 8,
   wherein said detector comprises a mechanically or electrically controllable polarizer, whose polarization angle can be mechanically or electrically changed.

10. The system as claimed in claim 8,
    wherein said detector comprises a rotatable polarizer, whose polarization angle can be changed by rotation of the polarizer, arranged in front of the detector input, at which the electromagnetic radiation is received.

11. The system as claimed in claim 8,
wherein said detector comprises an optical structure, whose polarization angle can be electrically controlled, arranged in front of the detector input, at which the electromagnetic radiation is received.

12. The system as claimed in claim 8,
further comprising a non-polarized radiation detector for detecting electromagnetic radiation reflected from the same skin region of the subject as the polarized radiation detector and for deriving additional detection data from the detected electromagnetic radiation,
wherein said device is configured to use said additional detection data as reference data used for selecting the optimum quality metric value from the determined quality metrics and for generating said polarization control information.

13. The system as claimed in claim 12,
wherein said non-polarized radiation detector comprises a plethysmography sensor configured for being mounted to a skin portion of the subject for acquiring photo-plethysmography signals and/or an imaging unit for acquiring a sequence of image frames of the subject over time, from which photo-plethysmography signals for use as reference data can be derived.

14. A method for extracting physiological information indicative of at least one vital sign of a subject from detected electromagnetic radiation reflected from the subject, said method comprising:
receiving a data stream of detection data derived from detected electromagnetic radiation reflected from a skin region of a subject, wherein the detected electromagnetic radiation is detected by a polarized radiation detector while the polarization angle of the polarized radiation detector is changed,
extracting a photoplethysmographic, PPG, signal from said detection data,
determining quality metrics from said PPG signal for different settings of the polarization angle of the polarized radiation detector,
selecting the optimum quality metric value from the calculated quality metrics,
generating polarization control information for use by said polarized radiation detector for setting the polarization angle to an angle value, at which said optimum quality metric value was obtained, for subsequent detection of radiation, and
deriving physiological information indicative of at least one vital sign from the PPG signal.

15. A non-transitory computer-readable medium carrying program code for causing a computer to carry out the steps of the method as claimed in claim 14 when said computer program is carried out on the computer.

16. An apparatus for extracting physiological information indicative of at least one vital sign of a subject from detected electromagnetic radiation reflected from the subject, said apparatus comprising:
a polarized radiation detector configured to detect electromagnetic radiation reflected from a skin region of a subject;
one or more computer processors configured to:
receive a data stream of detection data derived from the detected electromagnetic radiation detected by the polarized radiation detector while the polarization angle of the polarized radiation detector is changed,
extract a photoplethysmographic (PPG) signal from said detection data,
determine quality metrics from said PPG signal for different settings of the polarization angle of the polarized radiation detector,
select an optimum quality metric value from the calculated quality metrics,
generate polarization control information for use by said polarized radiation detector for setting the polarization angle to an angle value, at which said optimum quality metric value was obtained, for subsequent detection of radiation, and
derive physiological information indicative of at least one vital sign from the PPG signal; and
a display device configured to generate a display indicative of at least one of the derived physiological information and the at least one vital sign.

* * * * *